United States Patent [19]

Fischell

[11] Patent Number: 4,619,653

[45] Date of Patent: * Oct. 28, 1986

[54] APPARATUS FOR DETECTING AT LEAST ONE PREDETERMINED CONDITION AND PROVIDING AN INFORMATIONAL SIGNAL IN RESPONSE THERETO IN A MEDICATION INFUSION SYSTEM

[75] Inventor: Robert E. Fischell, Silver Spring, Md.

[73] Assignee: The Johns Hopkins University, Baltimore, Md.

[*] Notice: The portion of the term of this patent subsequent to Feb. 15, 2000 has been disclaimed.

[21] Appl. No.: 439,139

[22] Filed: Nov. 4, 1982

Related U.S. Application Data

[63] Continuation-in-part of Ser. No. 34,155, Apr. 27, 1979, Pat. No. 4,373,527.

[51] Int. Cl.⁴ .............................................. A61M 7/00
[52] U.S. Cl. .................................... 604/891; 604/151; 128/DIG. 13
[58] Field of Search ............... 128/DIG. 12, DIG. 13; 604/890–891, 65–67, 49, 131, 151–153

[56] References Cited

U.S. PATENT DOCUMENTS

| | | | |
|---|---|---|---|
| 3,672,352 | 6/1972 | Summers | 128/630 |
| 3,946,731 | 3/1976 | Lichtenstein | 604/66 |
| 4,037,598 | 7/1977 | Georgi | 128/DIG. 13 |
| 4,140,131 | 2/1979 | Dutcher | 128/419 PT |
| 4,191,181 | 3/1980 | Franetzki et al. | 128/DIG. 12 X |
| 4,308,866 | 1/1982 | Jelliffe et al. | 604/31 |
| 4,373,527 | 2/1983 | Fischell | 128/DIG. 13 X |
| 4,395,259 | 7/1983 | Prestele et al. | 604/67 |
| 4,405,318 | 9/1983 | Whitney et al. | 604/155 |
| 4,411,651 | 10/1983 | Schulman | 604/151 |
| 4,457,750 | 7/1984 | Hill | 604/65 |

OTHER PUBLICATIONS

Schubert, W. et al., "An Implantable Artificial Pancreas", MBE, vol. 18, 1980, pp. 527–537.

*Primary Examiner*—Kyle L. Howell
*Assistant Examiner*—Francis J. Jaworski
*Attorney, Agent, or Firm*—Robert E. Archibald; Howard W. Califano

[57] ABSTRACT

A medication infusion system provides redundant safety and includes condition detecting and informational alarm signal generating apparatus for indicating if (1) a fluid leak occurs in different portions of the system; (2) a programmable input from a patient or physician would result in exceeding a safe dosage limit; (3) the reservoir containing medication has been filled; (4) the intended medication pumping does not correlate with the pumping actually effected; (5) battery voltage is low; (6) the medication reserve is low; and (7) the system has been switched off. The apparatus may provide subcutaneous electrical, thermal, or audible stimulation to the patient and also provides a signal which a physician may monitor. The stimulation may be coded to separately identify each above-listed deviation in nominal system performance. In addition, the number of medication requests are correlated with actual medication dispensing to assure proper operation. An identification scheme is provided which matches the patient with his or her corresponding medication.

9 Claims, 9 Drawing Figures

APPARATUS FOR DETECTING AT LEAST ONE PREDETERMINED CONDITION AND PROVIDING AN INFORMATIONAL SIGNAL IN RESPONSE THERETO IN A MEDICATION INFUSION SYSTEM

STATEMENT OF GOVERNMENTAL INTEREST

The invention described herein was made in the performance of work under NASA Contract No. NDPR S-63983B and is subject to the provisions of Section 305 of the National Aeronautics and Space Act of 1958 (72 Stat. 435; 42 U.S.C. 2457).

REFERENCE TO RELATED CASES

This is a continuation-in-part of a patent application filed on Apr. 27, 1979 Ser. No. 34,155, now U.S. Pat. No. 4,373,527. The inventor in the related case was R. E. Fischell.

FIELD OF THE INVENTION

The present invention relates to apparatus for detecting selected conditions, including deviations in nominal performance, in a system for dispensing medication to a living being. Although mainly intended for use with human patients requiring infusions of a drug, such as insulin, morphine, heparin, or any of various other chemotherapeutic agents, the invention extends to use in any living body (such as domestic animals) and to the infusion of any liquid (such as blood) or colloidal suspension, or gas or granulated solid, which may be dispensed by the system and may provide a curative or healing effect. Although a principal use of the invention is in implantable devices, the principles of the invention also apply to systems external to a living being for the infusion of medication.

TECHNOLOGICAL CONTEXT OF THE INVENTION

Various techniques and devices have been suggested and are currently under study which address the problem of dispensing a drug or other medicative liquid into a living body. Of these techniques and devices, however, the provision of redundant safety features and the indication of certain vital operation conditions are rarely addressed and then to only a limited extent.

One liquid infusion device discussed in U.S. Pat. No. 4,077,405 by Haerten et al discloses a controllable dosing arrangement which provides for human operator interaction. A syringe forces liquid through a pressure valve into a supply reservoir and a bellows pump forces drug from the reservoir through a flow limiter into the body. The Haerton et al patent teaches an "overpressure" technique where liquid in the reservoir is at a pressure above that at the discharge point. This device fails to address various safety problems such as leakage, excessive pumping, and excessive requests for drug. In particular, should the input control valve in this patented device leak, a flood of liquid would enter the body because of the pressure differential and the lack of any back-up safety mechanism. No provision for detecting leaks in the device, for signalling selected deviation in nominal performance, for restricting the number of or quantity of drug doses, or for monitoring proper operation of the device is suggested.

Like Haerten et al, Ellinwood in U.S. Pat. No. 3,692,027 teaches an implanted, self-powered drug dispenser having a bellows pump which is fed through and expels drug through valves, in particular one-way valves. The Ellinwood device is not programmable; it varies dosage by opening and closing portals or selecting a dose of medication from one of a plurality of pumps having different dosage volumes and/or different medications stored therein. System operation relating to pressure integrity checks during filling, leakage problems, patient and doctor interaction with the dispenser, and dosage input programming, and informational outputs which correspond to such system operation conditions are not considered.

An invention of Blackshear (U.S. Pat. No. 3,731,681) shows another infusion pump without such features. While disclosing an implanted bellows pump arrangement fed through a self-sealing plug, the Blackshear pump does not look for pressure integrity before filling the device with drug. Further, because there is no input check valve and because the pressure in the device is above that of the body in which it is implanted, leakage in Blackshear can be dangerous. This is particularly true because the full reservoir will typically contain a lethal dose of medication if delivered over a short period of time. It is thus particularly significant that no means for indicating to a patient either proper or non-optimal performance is provided.

Richter (U.S. Pat. No. 3,894,538) considers, in a medicine supplying device, one safety feature: an exit plug for preventing contaminants from entering the device and for limiting drug outflow. However, redundant safety backed up by an informational signal providing feature is absent.

A device by Jacob (U.S. Pat. No. 4,033,479) provides a bellows pump which maintains drug in a chamber at a "constant internal pressure." A valve opens to release drug from the chamber into a body. The bellows varies the chamber volume to maintain constant pressure. It is not of importance to Jacob how much pressure there is in the chamber—it is above body pressure—but, rather, the concern is to keep pressure constant. Leakage out from the valve and the spurting of drug into the body under relatively high constant pressure would appear to be problems inherent in the Jacob device. Apparatus informing a patient of such conditions or other such conditions is not present.

Portner in U.S. Pat. No. 4,126,132 and its predecessor case, Ser. No. 599330 filed July 28, 1976, discuss the use of alarms in an intravenous delivery system. Sensors for detecting air in the delivery lines by making pressure measurements and sensors for detecting the amount of fluid in a supply bottle provide input to an audible or visual alarm. The use of alarms for a broad variety of conditions—which alarms would increase the safety of the system—is not discussed. Furthermore, the application of alarms to implantable medication release systems is not considered.

Franetzki et al U.S. Pat. No. 4,191,181 suggests the use of negative pressure, external to the medication reservoir, as a safety feature in a medication dispensing unit. However, this reference has no teaching of means for detecting and alerting the patient and/or physician regarding the structural and operational state of the unit, so as to provide information regarding e.g. leaks detected within the unit, excessive medication requests, stored medication level, blockage of the medication dispenser's output, etc.

Several recent publications have also underscored the advantages of a medication infusion device which is implantable. Two articles by Rhode et al ("One Year of Heparin Anti-coagulation;" *Minnesota Medicine;* October, 1977 and "Protracted Parenteral Drug Infusion in Ambulatory Subjects Using an Implantable Infusion Pump"; *American Society for Artificial Internal Organs Transactions, Volume XXIII;* 1977) describe an implantable infusion pump which comprises a hollow disk separated into two chambers by a bellows. A volatile fluorocarbon in the outer chamber forces drug from the inner chamber through a filter and catheter into a patient. Filling of the inner chamber is accomplished by penetrating a self-sealing septum which apparently forms a wall of the inner chamber. The condensation of the fluorocarbon provides energy for cyclical pumping. No antechamber, no check for pressure integrity before filling or during operation, no programming means, and no patient or doctor interaction with the device are contemplated. Detecting the status of such elements and providing corresponding informational signals are thus not considered.

Finally, an article by Spencer ("For Diabetics: an electronic pancreas;" *IEEE-Spectrum;* June, 1978) discusses current trends in the drug pump field. Preprogramming the rate of drug flow over time depending on food intake is mentioned. Efforts in the development of a bellows pump are also discussed. Spencer further mentions the use of alarm sounds if a pump fails to provide drug in accordance with the preprogrammed rate. The Spencer article generally discusses drug dispenser technology but fails to address many specific problems. As in other cited systems redundant safety features such as providing an antechamber; leak detection; providing distinctive subcutaneous stimulation or audio alarm to indicate various selected conditions and deviations in nominal performance; providing a safe method of programming the device regardless of work, food-intake, or time schedules; and maintaining the reservoir pressure below ambient body pressure so that a leak would result in body fluids entering the device as opposed to a fatal dose of drug entering the body (at a high, constant pressure) are not considered.

SUMMARY OF THE INVENTION

In a field where safety and reliability are paramount, the present invention provides extensive redundancy to prevent and, if appropriate, inform a patient of less than optimal system performance.

According to the medication infusion system described in the above-identified, related patent application, an antechamber is provided, which is filled with saline solution or a bacteriacidal solution or a non-lethal volume of the medication, to act as a buffer between the medication intake point and a medication reservoir in the device. The medication reservoir may contain a lethal dose of drug or other medication if released all at once. The input to the medication reservoir is thus isolated from the body by a filter, a one-way inlet valve, the antechamber and a septum which serves as a self-sealing opening to the antechamber. All of these elements are provided to prevent the leakage of medication from the medication reservoir into the body. As a further measure however, the medication reservoir is maintained at a pressure below the ambient body pressure. Thus, even if the inlet valve and septum leak, body fluids would enter the antechamber and ooze very slowly into the medication reservoir through the flow-impeding filter. A pressure build-up in the medication reservoir would be detected and an informational signal generated, indicating that the relative negative pressure in the medication reservoir had increased. On the one hand, the likelihood of a leak out is diminished and, on the other, the patient is informed if a leak out path exists. Further, any other leak to or from the medication reservoir would be sensed by a moisture detector outside the reservoir and an indicative informational signal generated.

Also at the outlet where medication from the medication reservoir is dispersed is an element for counting dispensed dosages of medication, which count can be compared to medication requests, thus providing an operational indicator and safety feature. If, for example, the pulsatile pump fails to function or its output is blocked (e.g. at the catheter), there will be a significant count discrepancy, and an informational signal will be provided. This feature would be of great significance in any medication infusion system whether the dispensing pump is implanted or external to the body.

In programming the medication infusion system, convenience and safety are major concerns. Thus, in addition to a programmable rate of medication input, a hardwired limit is also included to limit the dispensing of medication. If requests exceed the limits set by the program, the hardwired limits will inhibit the pulsing of excessive medication into the patient and an informational signal to the patient will be provided.

Safe filling is also a concern in the present invention. To assure that the patient receives the proper medication, a matching procedure of patient to medication is employed. If an identification code on the medication does not match a patient identification code, it will not be injected into the medication reservoir from which dispensing takes place. Like the bar coding of consumer products, a similar medication coding correlated to a patient and his needs is provided. An attempt at refilling a patient's unit with improper medication will prompt a warning signal to the physician. Filling the reservoir is also performed in a safe manner, with an indicator signal being activated when the reservoir is filled.

The informational signal to be provided when an improper operational condition is sensed can take various forms. A subcutaneous electrical, thermal, or acoustic signal in the form of a single pulse or multiple pulses which can have various pulse widths or pulse intervals can inform the patient of an existing or potentially undesired operating condition or proper operation if that is desired. In addition, provision is made for a physician to interrogate the medication infusion system to determine exactly what the condition is that is causing the alarm. For some patients the physician may wish to have the same informational signal provided for each different alarm with a unique signal (depending on the cause of the alarm) being made known by telemetry but only discernible by the physician.

The physician could also be provided with a means to disable any of the informational signals for a variety of reasons. For example, if the moisture detector became defective so that it incorrectly caused an informational (alarm) signal to be generated, then the physician may elect to turn that alarm off rather than surgically removing the device implanted in the patient. A telemetry means can be provided to determine which informational signals are enabled and which, if any, are disabled.

Various informational signals to indicate low battery voltage, medication reservoir nearly empty of medication, and medication infusion pump switched off are provided which could enhance the safe operation of an implanted or external pump in a medication infusion system. Additionally, indications are given when refill of the medication reservoir has been completed and if moisture is detected either between the reservoir and the outer casing or inside the compartment housing the electronics portion of the medication infusion system.

DESCRIPTION OF THE INVENTION

Figure 1:
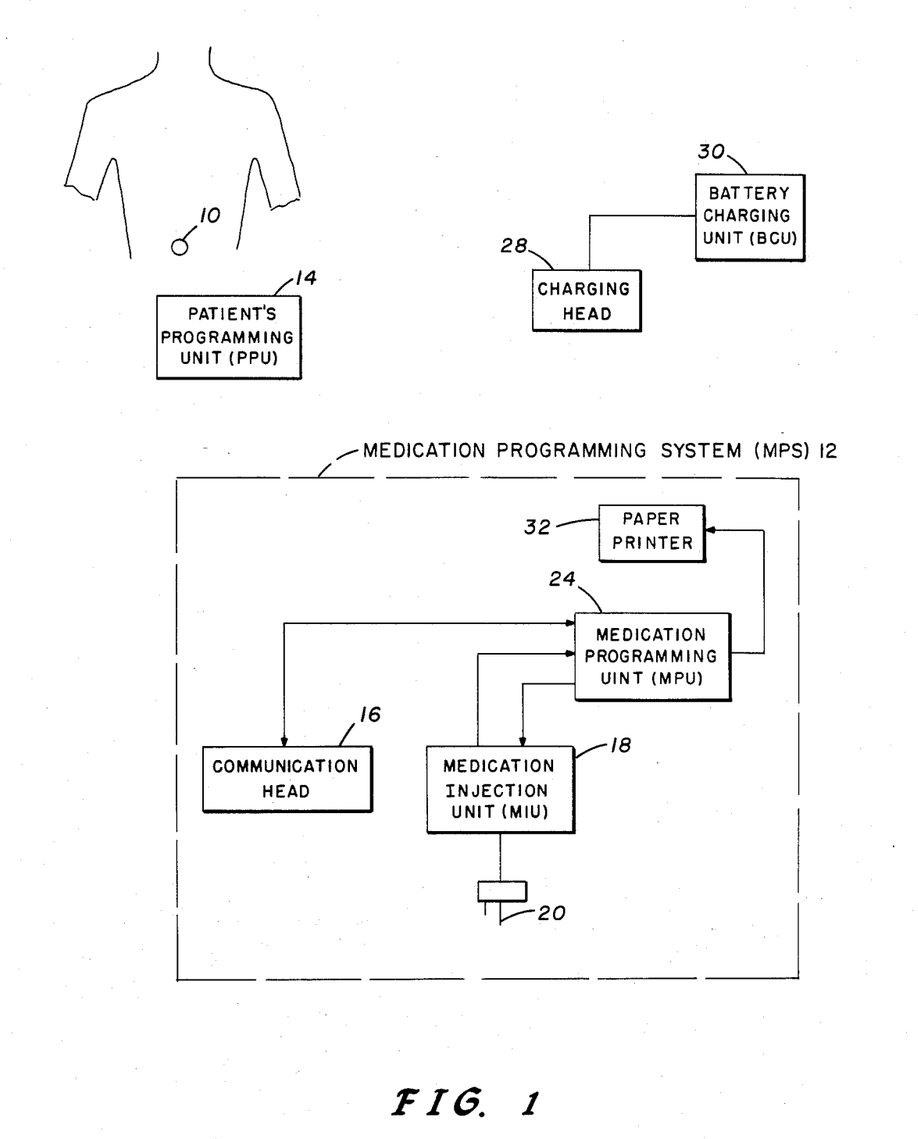
FIG. 1 is an illustration showing a general block diagram of a medication infusion system employing the present invention.

Referring to FIG. 1, the various portions of a programmable medication infusion system are shown. A medication dispensing unit 10 implantable in or external to a patient's body can be programmed either by the medication programming system 12 or by the patient's programming unit 14. Commands from the medication programming system 12 emitted from the communication head 16 are transmitted to electronics in the medication dispensing unit 10 in order to program and effectuate the infusion of medication into the body in a safe, controlled fashion. Furthermore, the communication head, 16, is used to receive signals telemetered out of the implanted unit 10. Thus, the communication head, 16 is really a command transmitting antenna and a telemetry receiving antenna. This antenna might typically be a few hundred turns of fine copper wire having approximately the same diameter as a similarly configured antenna in the implanted medication dispensing unit 10. The communication head 16, might also provide a source of an alternating magnetic field coupled to the similar coil in the implanted unit 10, to provide energy for recharging a rechargeable cell contained in 10. Furthermore the inductively coupled energy could be used to power the command and telemetry systems of the implanted unit 10.

The medication programming system 12 is also capable of reading information telemetered out from the medication dispensing unit 10, which information relates to the amount of medication dispensed over a specified time period as well as other data of value to the physician. Further, the medication programming system 12 is capable of calibrating the medication per pulse which is dispersed by the medication dispensing unit 10. A medication injection unit 18 is connected to a double hypodermic syringe 20 which is used to provide medication to a medication reservoir 22 (shown in FIG. 2) included within the medication dispensing unit 10. Fill commands to the medication injection unit 18 emanate from a medication programming unit 24. A patient's programming unit 14 (which may also communicate, by inductive transmission for example, with the medication dispensing unit 10) is controlled by the user (typically the patient) to request doses of medication, i.e. to obtain self-medication. The dispensing of dosage requests is limited by various elements included in the programmable memory units (shown in FIG. 8 as 106 and 108) and in the hardwired limit controls (shown at 110 and 112 in FIG. 8) all of which are found in the medication dispensing unit 10.

To recharge a power cell 26 (see FIG. 8) contained within the medication dispensing unit 10 (when the power cell 26 is a rechargable type), an external charging head 28 connected to a battery charging unit 30 is included. The need for the charging head 28 and battery charging unit 30 can be obviated by the inclusion in the medication dispensing unit 10 of a power cell 26 (such as a lithium cell) which is of sufficient lifetime to negate the need for recharging. Where the implantable portion 10 is, in fact, not implanted but is employed externally other methods of recharging or even replacement of the power cell may be employed. The medication programming unit 24 provides output to a paper printer 32 which provides hard, readable output that can be readily interpreted by a physician.

Figure 2:
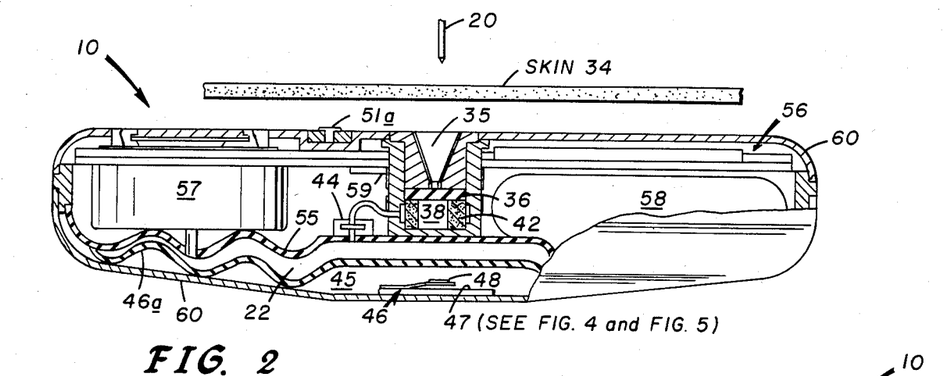
FIGS. 2 and 3 are illustrations showing a front cutaway and a top perspective view, respectively, of a medication dispensing unit in a medication infusion system.
Figures 3, 4, 5:
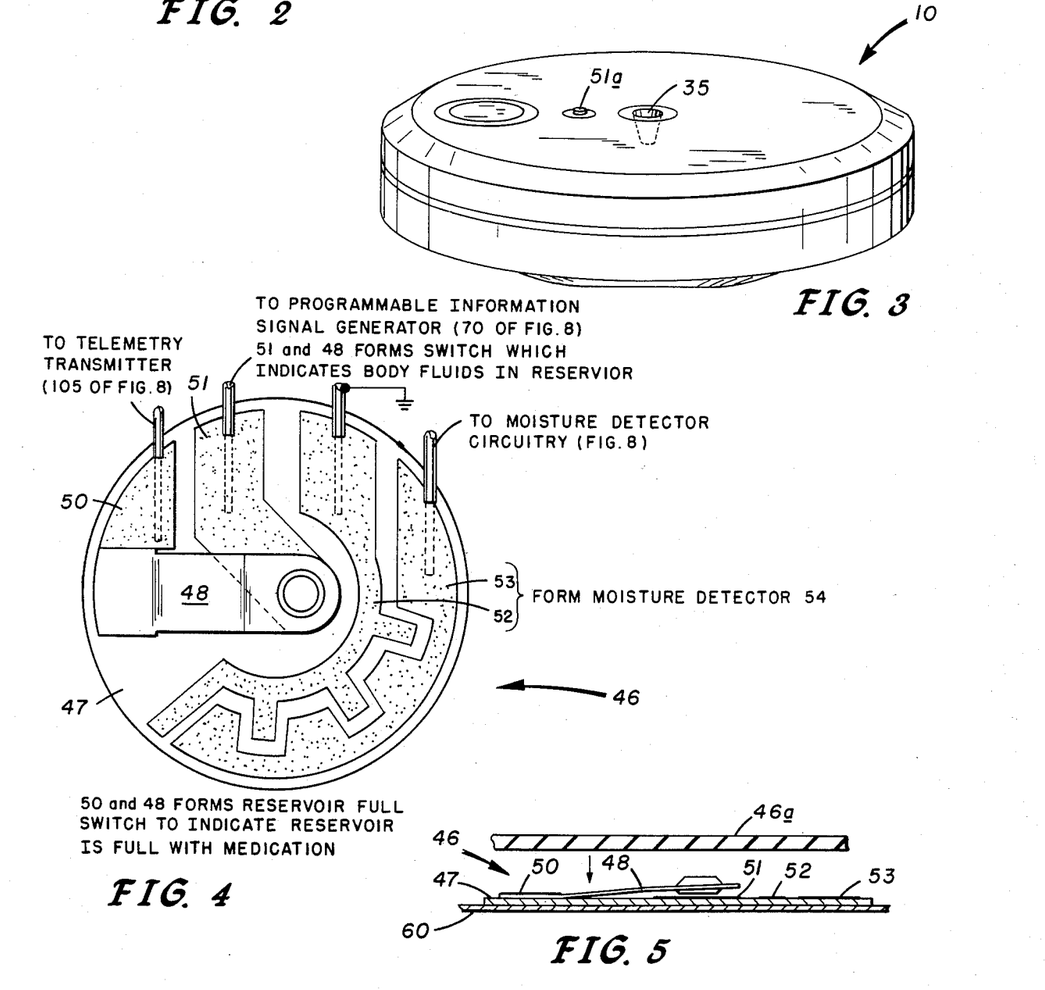
FIG. 4 shows, in detail, a top view of a combination moisture detector/switching unit which senses when various predetermined operating conditions exist.
FIG. 5 is a cross-section side view of the combination moisture detector/switch unit shown in FIG. 4.

Referring now to FIGS. 2 and 3, the medication dispensing unit 10 of an implantable programmable medication infusion system is shown. Medication is provided to the medication dispensing unit 10 by means of a hypodermic syringe 20 which penetrates the skin 34 and passes through a conical aperture 35 and a self-sealing septum 36, preferably made of medical grade silicone rubber or the like, which covers an antechamber 38 in leak-proof fashion. Medication is introduced into the antechamber 38 through syringe 20 at atmospheric pressure or under pressure the level of which is controllable externally. A medication reservoir 22, in which the medication is stored under relatively constant pressure, is fed from the antechamber 38 via a ceramic filter 42 and a one-way inlet pressure valve 44 which permits flow only from the antechamber 38 into the medication reservoir 22 when the pressure differential between them exceeds a predetermined threshold.

The inlet ceramic filter 42 surrounds the antechamber 38 and performs various functions which enhance the safety of the implantable portion 10 particularly in an implant environment. Besides filtering contaminants from medication being fed into the medication reservoir 22, the ceramic filter 42 serves to limit the rate of medication flow from the antechamber 38 into the reservoir 22 or, conversely, from the reservoir 22 into antechamber 38 should the inlet pressure valve 44 leak. Should the septum 36 leak, the ceramic filter 42 together with the inlet pressure valve 44 prevents the inflow of body fluids into the medication reservoir 22. Further, should the inlet pressure valve 44 and the septum 36 both leak or otherwise deviate from optimal performance, the filter 42 would permit only a slow flow of body fluids to enter the medication reservoir 22, until body ambient pressure is achieved, at which time some medication could diffuse through the ceramic filter 42 but at a rate that would not be hazardous to a typical patient in which the system would be implanted. Furthermore, when this occurs an informational signal would be generated.

A liquid-vapor pressurant chamber 45 is separated from medication reservoir 22 by a flexible diaphragm 46a. The liquid-vapor volume in the liquid-vapor chamber 45 preferably comprises a saturated vapor in equilibrium with a small amount of Freon 113 liquid. Over normal body temperatures, Freon 113 has a linear pressure characteristic ranging from −4 psig (at 98°) to approximately −2.5 psig (at 104° F.). Using Freon 113, the medication reservoir 22 will be maintained at a pressure below that of the human body pressure up to altitudes of 8500 feet. For patients who may live above that altitude, other fluorocarbons at lower pressure may be employed. In this way, should both the septum 36 and the inlet pressure valve 44 leak, the effect would be to cause body fluids to diffuse slowly through the inlet ceramic filter 42, into the medication reservoir 22 rather than to have a rapid flow of medication enter into the body where it could cause harm to the patient. Because of the pressure differential between the body and the medication reservoir 22, medication will not flow from the reservoir 22 into the body. As the amount of medication in the medication reservoir 22 varies, the flexible diaphragm 46a moves up or down, with the Freon 113 being converted either from liquid to vapor or vapor to liquid to provide an essentially constant pressure which will always be below one standard atmosphere and below normal body pressure. A medication reservoir 22 having a volume of approximately 10 cc would be sufficient for most applications. This amount of concentrated medication, insulin for example, could be fatal if injected over a short time. To prevent fatal leakage, the volume of the antechamber 38 is designed to have a safe dosage volume, e.g. less than 10% the size of the medication reservoir 22. In the worst case, if the medication reservoir 22 had a leak into the antechamber 38 which also had a leak, only medication diluted with incoming body fluids due to the pressure differential would initially enter the body. Such flow would be at a relatively slow diffusion rate because there would be zero pressure differential and because there is a very restrictive flow path. Under these conditions, the likelihood of leakage being fatal is minimized. As readily seen in FIG. 2, varying the size or shape of the medication reservoir 22 would be a simple modification because of the arrangement of elements in the system. A very important characteristic of the reservoir is that it is all metal (including the diaphragm 46a of FIG. 2.) so that no moisture can diffuse out of the reservoir 22 that could damage any of the electronics in the implanted unit 10.

Included in the liquid-vapor chamber 45 is a combined diaphragm position switch-moisture detector unit 46 (shown enlarged in FIGS. 4 and 5) comprising a ceramic insulator substrate 47 to which is attached a movable electrical contact 48, and deposited metal surfaces 50, 51, 52 and 53. When the medication reservoir is being filled, the flexible diaphragm 46a will move outward, and when the medication reservoir 22 is full, the flexible diaphragm 46a will make physical contact with the movable electrical contact 48. Since the flexible diaphragm 46a is preferably fabricated of metal and is therefore an electrical conductor, it will close an electrical circuit through the movable electrical contact 48 and the deposited metal surface 50 which can be used to send out a signal by the telemetering transmitter 105 of FIG. 8, to the medication programming system 12 of FIG. 7, to stop the infusion of medication.

If body fluids leak into the medication reservoir 22, the flexible diaphragm 46a will move out further, resulting in the movable electrical contact 48 being forced to make electrical contact with the metal surface 51 of FIG. 4. This switch closure would cause the programmable information signal generator 70 of FIG. 8 to provide an appropriate informational signal which would be sent to warn the patient. By way of example, the signal to the patient might be in the form of an electrical "tickle" stimulation applied subcutaneously by means of a stimulation electrode 51a of FIG. 8 disposed on the upper surface of the unit 10 (see FIG. 2). Another useful means for warning the patient would be by means of an acoustical transducer typically within the implanted device that would provide the patient with an audible alarm.

In the presence of Freon 113, but in the absence of moisture, the electrical resistance between the deposited metal surfaces 52 and 53 which collectively form the moisture detector 54 (see FIG. 8) is greater than 1 megohm. If however, moisture is released into the liquid-vapor chamber 45, either through a leaky flexible diaphragm 46a or if body fluids leak through the sealed outer cover 60 into the liquid-vapor chamber 45, then the moisture detector 54 will experience a detectable decrease in electrical resistance across the metal surfaces 52 and 53. If this occurs, moisture detector 54 initiates an informational signal to be sent to the patient to indicate a leak in the implanted unit 10.

Figure 7:
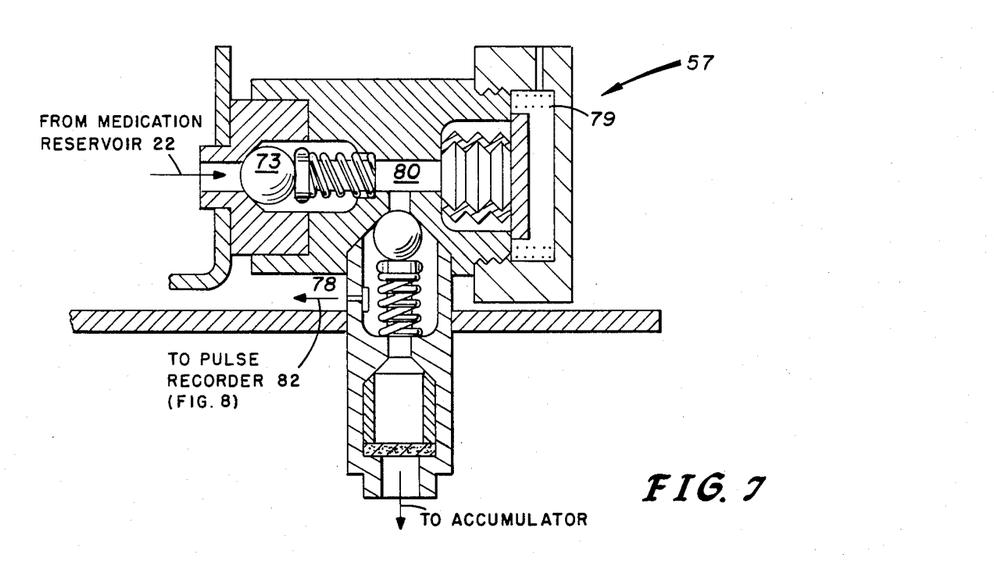
FIG. 7 is a cross-section view of one embodiment of a pump which may be included in the present system.

The medication reservoir 22 and liquid-vapor chamber 45 are separated from the other portions of the medication dispensing unit 10 by wall 55 (forming the top of reservoir 22, as viewed in FIG. 2) and fluidically isolated from the other elements of the system by means of the inlet pressure valve 44 and a pump inlet valve 73 (see FIG. 7) which connects the reservoir 22 to a pulsatile pump 57 (shown in detail in FIG. 7). The remaining elements of the implantable medication dispensing unit 10 are shown in FIG. 2 above and isolated from the reservoir 22 (by wall 55) and include an electronics compartment or section 56 containing a power cell subsection 58. As is readily seen in FIG. 2, an outer cover 60 isolates the medication reservoir chamber 22 and liquid-vapor pressurant chamber 45 as well as the pump 57 and the electronics compartment or section 56 (and the power cell subsection 58) from the external environment. A moisture detector 59, of the same design as detector 54 described above, would be located in an electronics section 56 (of FIG. 2) so that it could detect and provide an informational signal to the patient if either a medication leak occurs through the wall 55 or body fluids penetrate the top portion of the sealed outer cover 60.

Figure 6:
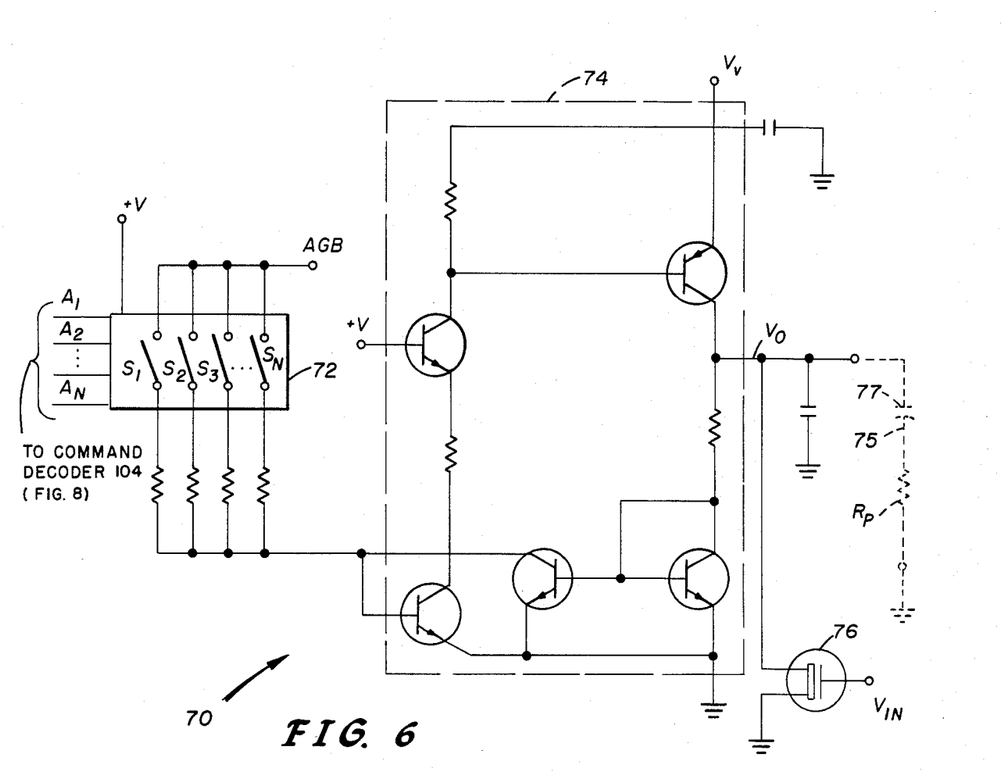
FIG. 6 shows one embodiment of an informational signal generator.

An informational signal generator 70, such as that shown in FIG. 6, can be used in signalling or alerting a patient of a predetermined condition or in checking the medication dispensing unit 10 (of FIG. 2). The generator 70 has a plurality of inputs $A_1$ through $A_N$. The $A_1$ through $A_N$ inputs are provided by a command decoder (104 of FIG. 8), the inputs $A_1$ through $A_N$ selectively switching elements $S_1$ through $S_N$ in amplitude select element 72 to provide $2^N$ possible, programmable voltage levels. The programmable voltage level is applied to an amplifier transistor circuit 74, which is biased by a voltage $V_A$. The output signal $V_o$ of the circuit 74 can be applied to a lead 75 in contact with the patient if an input ($V_{IN}$) to a FET 76 is provided. A capacitor 77, preferably of one microfarad, is located between the alarm output signal $V_o$ and the patient to generate a patient-sensed voltage across load $R_p$ ranging between one and ten volts selectable in programmable steps. The load $R_p$ can provide electrical stimulation (e.g. by means of the stimulation electrode 51a in FIG. 2), heat, or audio alarm output to inform the patient. In the case of an informational (alarm) signal provided by electrical stimulation, the load $R_p$ is the electrical load caused by the patient's tissue and fluid surrounding the alarm electrode 51a. When the FET 76 conducts, the load $R_p$ is short-circuited. When the FET 76 is not conducting (there is no $V_{IN}$), a stimulating signal through the load $R_p$ can be effected. The information signal generator 70 input $V_{IN}$ may be high (or "on") when any one of a plurality of selected conditions is detected and signalled, such as: the fill limit of reservoir 22 has been reached (when diaphragm 46a connects to switch contact 48 in FIG. 5), body fluids have entered reservoir 22 (when contact 48 connects to surface 51), unwanted moisture has been detected within the unit 10 (by detector 54 or 59 in FIG. 8), and the like.

The pump 57 shown in FIG. 7 is discussed in detail in the above-referenced patent application. In an output chamber of the pump 57 is a transducer 78 which senses when a pulsatile dose of medication is dispensed. Transducer 78 detects pressure build-up in the output chamber of pump 57. It may be noted that other types of transducers are available which can detect a pulsatile flow through an output tube. Each pulse of medication is communicated by the transducer 78 as an electrical pulse and therefore, based upon prior knowledge of the volume of medication in reservoir 22 when full and the volume of medication dispensed for each actuation of pump 57, it is obvious that at any given time the current volume of medication remaining in the reservoir 22 can be determined by merely recording a count of the number of pulses produced by transducer 78. To promote a pulse of medication, a coil 79 (or other similar means of reciprocating a variable volume pump storage chamber 80) is provided with a pulse of electrical energy.

By comparing the number of electrical pulses to the coil 79 with the number of electrical pulses produced by the transducer 78, an operational check is performed and indicates, for example, that the output of the medication dispensing system is clogged. Thus, as seen in FIG. 8, electrical pulses from the transducer 78 and a count of electrical pulses to the coil 79 are communicated to and stored in a pulse recorder 82.

The output of the transducer 78 is also applied to a pulse rate detector 84. The pulse rate detector 84 provides a hard-wired "insufficient rate" command input which provides a programmable lower medication dispensing limit. That is, when less than a physician prescribed minimum of medication is delivered to the body, the rate detector 84 signals information signal generator 70 that an informational (alert) signal to the patient is to be generated. To effect this signal, an input (line 84a) to the programmable information signal generator 70 (of FIGS. 6 and 8) is connected through switch inputs, such as $V_{IN}$ in FIG. 6. Although shown as a FET switch input, $V_{IN}$ may provide input to another form of switch connected to a programmable information signal generator 70 which may have a pulse coded memory and varied outputs corresponding to inputs for different conditions (as shown in FIG. 8.) Overpressure (from an over-filled reservoir), fluid detection, pulse count discrepancy, excessive pulse request, low battery voltage, and the like can thus stimulate an alarm signal by entering a line like $V_{IN}$ of FIG. 6.

For example, the pulse rate detector 84 sends transducer pulse rate information to the pulse recorder 82, which information is compared by comparator circuitry in the pulse recorder 82 to the electrical pulses over the same period from the coil 79. A discrepancy between the two counts results in a signal to the information signal generator 70 over line 82a, as seen in FIG. 8 which causes the FET 76 (FIG. 6) to assume a high impedance state and a current to pass through stimulation electrode 51a. As noted earlier, thermal, acoustic, or other similar stimulation to the body might be used in place of or in combination with the electrical stimulation.

Figure 8:
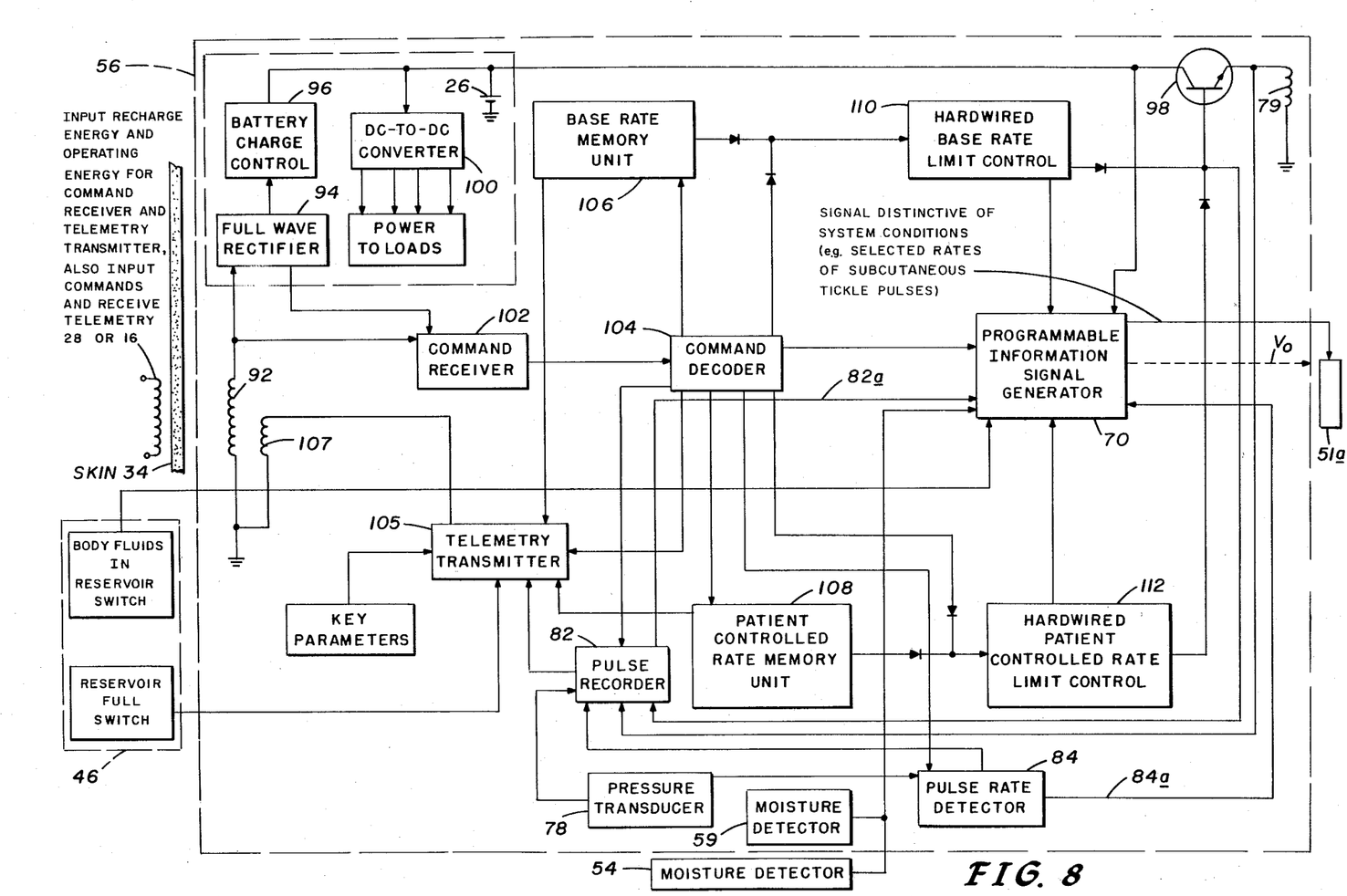
FIG. 8 is a block diagram showing electronic components of the system.

As seen in FIG. 8, the electronics portion of medication dispensing unit 10 (enclosed by dashed line 56 of FIG. 8) communicates with a communication head 16 which is external to the body (for both implanted and external embodiments). Communication may be by wire for external embodiments or, for implantable or external embodiments, by radiant energy (in electromagnetic, alternating magnetic, or other remote signal forms).

The communication head 16, in the FIG. 8 embodiment, provides both power and command inputs, as well as receiving telemetry output. More specifically, input power is provided by means of an alternating field, e.g. a magnetic field, which is communicated to a pickup coil 92 which is connected to other elements of the electronics section 56. The pickup coil 92 receives a power signal and passes it on to a full wave rectifier 94. One rectified output from the full-wave rectifier 94 enters a battery charge control 96 which provides a fixed DC charging signal to a power cell 26. The power cell 26 can be a nickel-cadmium cell which is readily rechargeable off a rectified signal at a typical frequency of 20 kHz. Alternatively, a lithium-type solid state battery can be used instead of the nickel-cadmium cell in which case the charging circuitry could be eliminated, the lithium-type battery providing sufficient power over a long term, thereby obviating the need for recharging. The power cell 26 provides a biasing voltage to a switch 98, the output of which enters the pulsing coil 79 previously described.

In addition to providing power to the power cell 26, rectified power is also introduced to a DC-to-DC converter 100 the purpose of which is to provide power at the proper levels to the various loads in the system. In addition to the AC power signal, pickup coil 92 may also receive a train of serial digital bits, e.g. from the communication head 16. The digital bits comprise commands for programmable inputs which are conveyed, via the pickup coil 92 to a command receiver 102. The signals from the command receiver 102 enter a command decoder 104 which determines if the digital bits are in a proper format and, if so, what action in the system the commands dictate. To allow remote verification of the information decoded in command decoder 104, the decoded signals are transmitted back to the communication head 16 by means of a telemetry transmitter 105 and a telemetry coil 107. It should also be noted that the full wave rectifier 94, the battery charge control 96, the command receiver 102, the command decoder 104 and telemetry transmitter 105 could be powered only when an AC signal is picked up by the pickup coil 92. As seen in FIG. 8, for example, the command receiver 102 receives operating power from the full-wave rectifier 94 enabling it to convey signals from the coil 92 to the command decoder 104. It should be obvious that a power savings is achieved by only powering the command receiver etc. when necessary and, moreover, prevents the possibility of detecting stray signals as commands. To be sure, the power savings achieved could make possible the use of the aforementioned lithium cell which would not require recharging.

From the command decoder 104, programmable inputs and other commands can be provided to a number of elements. A programmable base rate is entered into a base rate memory unit 106 which stores a value indicating the number of pulses of medication which are to be provided to a patient during a normal preselected period of time. A second programmable input is provided to a patient-controlled rate memory unit 108 which stores a value indicating a number of pulses of medication that are requested by the patient (with a patient programming unit 14) to be introduced into the body.

Associated with the base rate memory unit 106 is a hardwired base rate limit control 110 which sets a maximum rate that can override requests of the base rate memory unit 108 which are excessive. Similarly, a hardwired patient-controlled rate limit control 112 provides a fixed maximum number of pulses which can be provided at a time after a meal or at other times and under other conditions such as exercise. As long as the base rate and patient-controlled rate values stored in memory units 106 and 108 respectively, do not exceed the hardwired values fixed within limit controls 110 and 112, respectively, an output pulse is provided to the switch 98 to stimulate a pulse output from pulsing coil 79. Should the rate of either memory unit 106 or 108 exceed the hardwired limits in the limit control elements 110 or 112, respectively, a "rate request exceeds limit" signal is fed from the limit control element 110 or 112 into the programmable information signal generator 70 which provides an electrical signal to the load $R_p$. The patient (in one form of the invention) is informed by means of a stimulation that more medication than permitted has been requested.

It should be noted that the signal to the load $R_p$, e.g. an electrode, can serve the dual function of not only providing the patient with a subcutaneous, heat, or audible stimulation but may also be detected by the communication head 16, via signal transfer means $V_o$, and may be communicated to the physician, thereby indicating that a deviation from optimal system status has occurred. As shown in FIG. 8, the load $R_p$ will be isolated and electrically insulated from the outside of the enclosure 60 of the medication dispensing unit 10.

A particularly significant feature of the invention resides in the programmability of the information signal generator 70 based on input commands from the command decoder 104. The voltage produced by the signal generator 70 across the load $R_p$ can be varied in response to signals emanating from the communication head 16 and channelled through the command receiver 102 to the command decoder 104 and into inputs $A_1$ through $A_n$ of amplitude select element 72 (shown in FIG. 6).

In addition, in order to check the proper operation of the system, the command decoder 104 can receive test signals which can stimulate actual occurrences to determine whether the circuitry in the electronic section 56 is operating properly. For example, extra pulses from the command decoder 104 can be entered into the hardwired limit control elements 110 and 112. These extra pulses can be added to the pulses provided by the base rate and the patient-controlled rate memory units 106 and 108, in order to exceed the hardwired base rate and the hardwired patient-controlled rate, respectively. When the rates are exceeded, the information signal generator 70 will provide a signal. In this way, the information signal generator 70 can be used to check the operation of the limit control elements 110 and 112, inform the physician of operational problems via means $V_o$, and also familiarize the patient with the corresponding stimulation emitted by the load $R_p$.

The programmable information signal generator 70 also receives inputs from the movable electrical contact 48 and the moisture detectors 54 and 59 (see FIGS. 2 and 4). If body fluids leak into the medication reservoir 22, the movable electrical contact 48 will make electrical contact with 51, indicating this fault condition to the patient by activating the information signal generator 70. If the patient was unconscious, voltage levels on the patient's skin at the site of the medication dispensing unit 10 could be used by the physician to detect if a deviation has occurred and could, with a pulse-coded embodiment, indicate which selected deviation in nominal performance it was. Further, as previously described, should fluid leak out of the medication reservoir 22 or if body fluid should leak in through the enclosure 60, the moisture detector 54 would sense such leakage and, as shown in FIG. 8, would provide input to the information signal generator 70. Similarly, moisture detector 59 would signal the presence of medication or body fluid in the electronics compartment 56. Still another input to the information signal generator 70 comes from the power cell 26 associated with the transistor switch 98. The voltage level of the power cell 26 is thus communicated to the signal generator 70; a stimulation signal being generated when the battery voltage is below a predetermined level.

It should be noted that the various mentioned conditions in the system result in stimulations each of which may all be the same or which may be different in stimulation pulse amplitude, duration, periodicity, interpulse spacing or other coding. For example, the stimulation may range between one to ten volts; may vary in frequency over a wide range; and, most importantly, a variety of unique pulse patterns may be used to indicate the various selected conditions or deviations in nominal performance.

As discussed previously, additional signals to initiate an informational signal to the patient are derived from pulse count information in the pulse recorder 82 and pulse rate detector 84 of FIG. 8 and might also be derived from any of a variety of optical, capacitive, inductive, liquid crystal, or other reservoir level measuring elements which might be utilized to inform the patient (or physician) when say only 10% or a 5 days supply of the medication remains in the reservoir.

Figure 9:
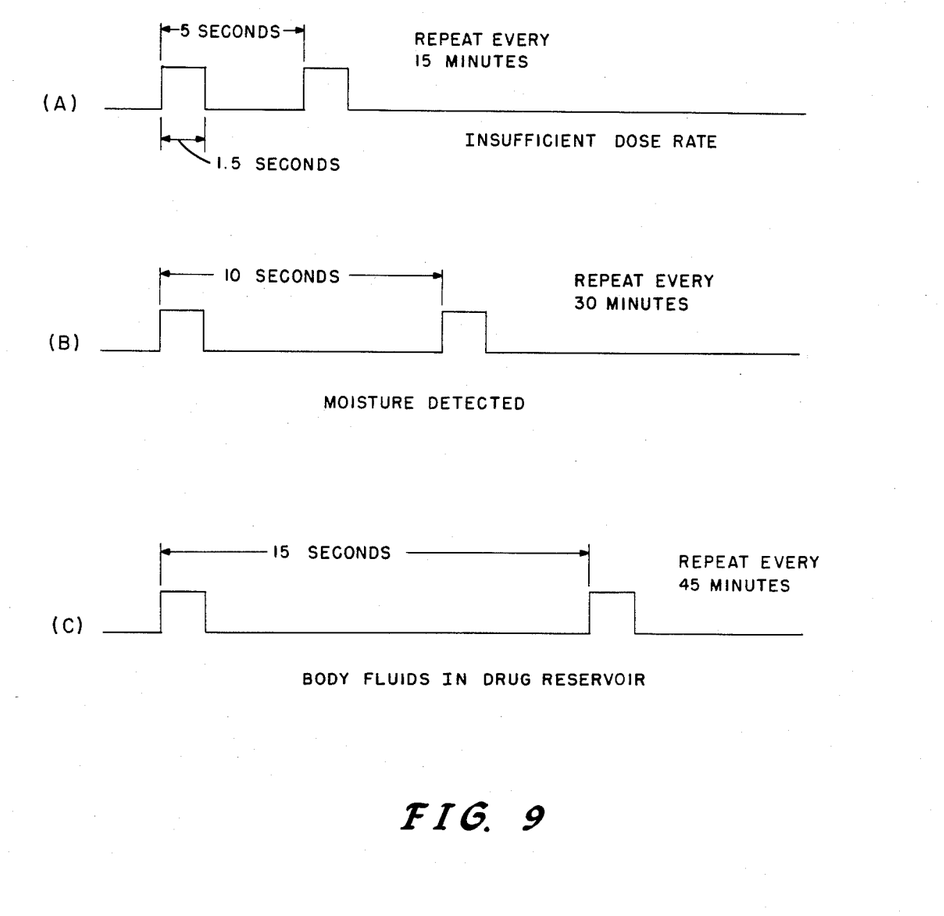
FIG. 9 shows signals representing various pulse-coded alarm patterns used in informing a patient of various deviations from normal operating conditions.

Referring to FIG. 9, three pulse-coded deviation signals are illustrated. In FIG. 9(A), two 1.5 second signals five seconds apart are repeated at fifteen minute intervals to indicate insufficient medication rate. In FIG. 9(B), two 1.5 second signals ten seconds apart are repeated at thirty minute intervals to indicate a moisture leak. In FIG. 9(C), two 1.5 second signals fifteen seconds apart are repeated every forty-five minutes to indicate that the medication reservoir contains body fluids. Similar coding or a variation thereof can also be employed to indicate low battery voltage and undesirably high medication rate requests.

It may also be desirable to have the same pattern for all alarms, but have a unique informational signal be provided only for the physician to determine the specific cause of that alarm. If that was done, then any one of the signal formats of FIG. 9 could be used as the alarm pattern for the patient.

Various other modifications, adaptations and alterations are of course possible in light of the above teachings. Therefore, it should be understood at this time that within the scope of the appended claims the invention may be practiced otherwise than as specifically described.

What is claimed is:

1. An infusion system for providing medication to a living body of a patient comprising:
   an infusion apparatus for implantation in said living body, including,
      a medication reservoir for storing selected medication;
      a pump means for infusing a fixed dosage of said medication into said living body with each pump actuation;
      an infusion output from which doses of medication exit the infusion apparatus and are dispensed to the patient;
      a control means for applying an electrical pulse to the pump means to delivery said fixed dosage of medication;
      a means for detecting the presence of at least one predetermined condition regarding the operational state of the infusion apparatus, wherein said detecting means comprises a condition sensor, disposed at the infusion output, for sensing the dispensing of a dose of medication, and, a comparing means for detecting when the number of medication dosages detected by said condition sensor deviates from the number of applied electrical pulses generated by said control means; and,
      a means, operably coupled to said detecting means, for alerting said patient when said at least one predetermined condition is detected.

2. An infusion system for providing medication to a living body of a patient comprising:
   an infusion apparatus for implantation in said living body, including,
      a medication reservoir for storing selected medication;
      a means for maintaining the pressure in the medication reservoir below a predetermined level that is less than ambient body pressure;
      a means for detecting the presence of at least one predetermined condition regarding the operational state of the infusion apparatus, wherein said detecting means comprises a condition sensor for detecting when the fluid level in the reservoir exceeds a predetermined fill level higher than a normal full level, indicating that body fluids have leaked into the infusion apparatus; and,
      a means, operably coupled to said detecting means, for alerting said patient when said at least one predetermined condition is detected.

3. The apparatus as in claim 2, wherein said detecting means further includes a second condition sensor for detecting when the pressure in the medication reservoir exceeds a predetermined pressure level.

4. The apparatus of claim 1 or 2, wherein said alerting means comprises:
   an acoustic transducer; and,
   a means, responsive to said detecting means, for activating said acoustical transducer to generate an acoustical signal when said at least one predetermined condition is detected.

5. The apparatus of claim 1 or 2, wherein said alerting means comprises:
   a tickle means for applying a subcutaneous electrical tickle to an intracorporeal location; and,
   a means, responsive to said detecting means, for activating said tickle means to generate an electrical tickle when said at least one predetermined condition is detected.

6. An infusion system for providing medication to a living body of a patient comprising:
   an infusion apparatus for implantation in said living body, including,
      a medication reservoir for storing selected medication;
      a means for detecting the presence of at least one predetermined condition regarding the operational state of the infusion apparatus;
      a tickle means for applying a subcutaneous electrical tickle to an intracorporeal location; and,
      a patient alerting means, responsive to said detecting means, for activating said tickle means to generate an electrical tickle when said at least one predetermined conditions is detected, wherein said infusion system contains an extracorporeal transmitter for sending a command signal to set the intensity of said electrical tickle and wherein said infusion apparatus further includes a receiver means operably coupled to said patient alerting means for detecting said command signal and wherein said patient alerting means includes a means for setting the intensity of said electrical tickle in response to said received command signal.

7. An infusion system for providing medication to a living body of a patient comprising:
   an infusion apparatus for implantation in said living body, including,
      a medication reservoir for storing selected medication;
      a means for detecting the presence of at least one predetermined condition regarding the operational state of the infusion apparatus;
      an acoustical transducer;
      a patient alerting means, responsive to said detecting means, for activating said acoustical transducer to generate an acoustical signal when said at least one predetermined condition is detected, wherein said infusion system contains an extracorporeal transmitter for sending a command signal to set the intensity of said acoustical signal and wherein said infusion apparatus further includes a receiver means operably coupled to said patient alerting means for detecting said command signal and wherein said patient alerting means includes a means for setting the intensity of said acoustical signal in response to said received command signal.

8. An infusion apparatus for implantation into a living body of a patient comprising:
   a housing;
   a medication reservoir for storing selected medication, said medication reservoir located in said housing;

a pump means for infusing a fixed dosage of said medication into said living body with each pump actuation;
an infusion output coupled to said pump means from which dosages of medication exit the infusion apparatus and are dispensed into the patient;
a control means for applying electrical pulses to said pump means, each electrical pulse actuating said pump means to deliver said fixed dosage of medication;
a power supply;
a means associated with said medication reservoir for maintaining the pressure in said medication reservoir below a predetermined level that is less than ambient pressure;
a means for monitoring at least two predetermined conditions regarding the operational state of the infusion apparatus, said at least two conditions selected from the following group of conditions:
 a. medication level in said medication reservoir is at a preselected low level,
 b. presence of medication or body fluids between the medication reservoir and the housing,
 c. a difference between the number of electrical pulses provided by said control means to said pump means and the number of fixed dosages of medication delivered by said pump means through said infusion output;
 d. medication level in said medication reservoir exceeds a predetermined fill level higher than a normal full level, indicating that body fluids have leaked into the infusion apparatus,
 e. pressure in the medication reservoir exceeds a predetermined negative pressure level, and
 f. power supply output falls below a preset level,
an acoustical transducer; and,
a patient alerting means, responsive to said monitoring means for activating said acoustical transducer to generate an acoustical signal when at least one of said predetermined condition is detected.

9. An infustion apparatus for implantation into a living body of a patient comprising:
a housing;
a medication reservoir for storing selected medication, said medication reservoir located in said housing;
a pump means for infusing a fixed dosage of said medication into said living body with each pump actuation;
an infusion output coupled to said pump means from which dosages of medication exit the infusion apparatus and are dispensed into the patient;
a control means for applying electrical pulses to said pump means, each electrical pulse actuating said pump means to deliver said fixed dosage of medication;
a power supply;
a means associated with said medication reservoir for maintaining the pressure in said medication reservoir below a predetermined level that is less than ambient pressure;
a means for monitoring at least two predetermined conditions regarding the operational state of the infusion apparatus, said at least two conditions selected from the following group of conditions:
 a. medication level in said medication reservoir is at a preselected low level,
 b. presence of medication or body fluids between the medication reservoir and the housing,
 c. a difference between the number of electrical pulses provided by said control means to said pump means and the number of fixed dosages of medication delivered by said pump means through said infusion output;
 d. medication level in said medication reservoir exceeds a predetermined fill level higher than a normal full level, indicating that body fluids have leaked into the infusion apparatus,
 e. pressure in the medication reservoir exceeds a predetermined negative pressure level, and
 f. power supply output falls below a preset level,
a tickle means for applying a subcutaneous electrical tickle to an intracorporeal location; and,
a patient alerting means, responsive to said monitoring means, for activating said tickle means to generate an electrical tickle when at least one of said predetermined conditions is detected.

* * * * *